United States Patent [19]

Shiue et al.

[11] 4,439,414

[45] Mar. 27, 1984

[54] 1-$^{11}$C-D-GLUCOSE AND RELATED COMPOUNDS

[75] Inventors: Chyng-Yann Shiue, Wading River; Alfred P. Wolf, Setauket, both of N.Y.

[73] Assignee: The United States of America as represented by the United States Department of Energy, Washington, D.C.

[21] Appl. No.: 342,684

[22] Filed: Jan. 26, 1982

[51] Int. Cl.$^3$ ............................................. A61K 49/02
[52] U.S. Cl. ..................................... 424/1.1; 250/303; 128/1.1; 128/659; 127/30; 536/1.1
[58] Field of Search ......................... 424/1; 252/301.1; 260/429.1; 128/1.1, 659; 250/303; 127/30; 536/1.1

[56] References Cited

PUBLICATIONS

Shiue, C-Y., et al., Carbohydrate Research, vol. 74, pp. 1–4 (1979).
Raichle et al., Science, vol. 199, pp. 986–987 (1978).
Wolf et al., Radiopharmaceuticals & Labelled Compounds, vol. 1, pp. 345–381 (1973).
Heindel, N. P. et al., Chemistry of Radiopharmaceuticals, pp. 109–122, Mason Publishing, N.Y. (1978).
Depresseux, J. C. et al., European Neurology, vol. 20, pp. 270–272 (1981).
Goulding, R. W. et al., Internat. J. Applied Radiation & Isotopes, vol. 24, pp. 7–12 (1973).
Lifton, J. F. et al., Radiation Research, vol. 45, pp. 35–40 (1971).

*Primary Examiner*—Benjamin R. Padgett
*Assistant Examiner*—M. Moskowitz
*Attorney, Agent, or Firm*—Margaret C. Bogosian; Paul A. Gottlieb

[57] ABSTRACT

The novel compounds 1-$^{11}$C-D-glucose, 1-$^{11}$C-D-mannose, 1-$^{11}$C-D-galactose, 2-$^{11}$C-D-glucose, 2-$^{11}$C-D-mannose and 2-$^{11}$C-D-galactose which can be used in nuclear medicine to monitor the metabolism of glucose and galactose can be rapidly prepared by reaction of the appropriate aldose substrate with an alkali metal $^{11}$C-labeled cyanide followed by reduction with a Raney alloy in formic acid.

6 Claims, No Drawings

1-$^{11}$C-D-GLUCOSE AND RELATED COMPOUNDS

BACKGROUND OF THE INVENTION

The United States Government has rights in this invention pursuant to Contract Number DE-AC0276CH00016 between the United States Department of Energy and Associated Universities, Inc.

This invention relates to novel 1-, 2-$^{11}$C-labeled aldohexoses and to methods for preparing them. More specifically, the invention relates to novel radiopharmaceuticals such as 1- and 2-$^{11}$C-D-glucose, mannose and galactose and to a new method of preparing and isolating such compounds.

The rapid development and advancement in the technology of computerized tomography has made it possible to study the dynamic properties of radiopharmaceuticals in vivo, non-invasively and quantitatively. Two major and related approaches have been used in the design of radiopharmaceuticals. These are, (1) targeting of the radiopharmaceutical to a particular organ by taking advantage of its unique metabolism or function, and (2) the use of labeled substrates to map metabolic activity or primary events which lead to a biological response in the case of drugs. Based on these ideas, a number of organ specific radiopharmaceuticals have been synthesized.

The compound $^{18}$F-2-deoxy-2-fluoro-D-glucose has been shown to be an effective tracer for quantitatively mapping the first step of glycolysis in the brain and heart. It has also been used in the study of psychiatric conditions of patients. However, it is an analog of glucose rather than the naturally occurring substance. It has been suggested that with analogs corrections must be made in the tracer model to allow for differences in transport properties and enzyme affinities between the naturally occurring product and its analog. Furthermore, some naturally occurring products metabolize differently in afflicted patients compared with normal subjects. For example, D-glucose has been shown to metabolize differently in psychotic patients and normal subjects. The metabolism of D-mannose is similar to that of D-glucose.

The metabolism of D-galactose is of interest for the study of galactosemia of human infants. This metabolic malfunction is characterized by insufficient levels of the enzyme phosphogalactose uridyl transferase which is essential for the proper metabolism of galactose. Excessively high concentration of D-galactose in the blood of human infants has been associated with cataracts of the lens of the eye and with mental disorders.

It has therefore, been of interest to prepare radiolabeled D-glucose and D-mannose and D-galactose for use in computerized tomography.

Carbon-11 labeled glucose has been synthesized by a biosynthetic method (Lifton et al: Radiat. Res. 45:35–40, 1971; Straatman et al: Int. J. Appl. Radiat. Isot. 24; 234–236, 1973 and Wolf: Radioisotopy 12:499–518, 1971). However, there are several problems associated with this method. These are (1) the glucose is randomly and not necessarily uniformly labeled, (2) it is necessary to separate glucose from plant residue, particularly the removal of pyrogens and other biologically active compounds. C-11 labeled glucose has also been synthesized utilizing algae as the biosynthetic medium (Ehrin et al: J. Label Comp. Radiopharm. 17:453–461, 1980). However, the $^{11}$C-D-glucose is still randomly labeled.

Glucose, mannose and galactose have been synthesized by numerous methods. The classical synthesis of Emil Fischer involves the addition of one carbon atom to an aldose molecule by reaction of the aldose substrate with sodium cyanide followed by conversion of the cyano or nitrile group to an aldehyde group by any of a number of known methods. Two epimers in which the hydroxyl group and hydrogen atom attached to the number two carbon atom are oppositely arranged on that atom are obtained.

Recently Serianni et al have reported the use of the Fischer synthesis to produce $^{13}$C-D-glucose from aldonitriles followed by palladium catalyzed reduction with hydrogen (Carbohydrate Res. 72:71–78, 1979; J. Org. Chem. 45:3329–3341).

These methods, however, are time consuming. For example, the synthesis of 1-$^{14}$C-D-glucose took more than two days and the hydrogenolysis of aldonitriles to aldoses took more than two hours. The procedures obviously are not sufficiently rapid to permit the synthesis of glucose labeled with the $^{11}$C isotope which has a half life of only 20.4 minutes.

SUMMARY OF THE INVENTION

One object of this invention is to produce the novel radiopharmaceuticals 1-$^{11}$C-D-glucose, 2-$^{11}$C-D-glucose, the corresponding mannose compounds, 1-$^{11}$C-D-galactose and 2-$^{11}$C-D-galactose.

Another object of this invention is to utilize the aforesaid compounds as diagnostic agents, more specifically for mapping the course of glucose metabolism, for example, in the brain and heart, and for following galactose metabolism in the human body.

Another object of this invention is to synthesize the aforesaid compounds by a rapid technique utilizing radioisotopes which have a sufficiently long half life to permit the completion of positron emission tomographs without unnecessarily producing a high radiation burden for the individual patient.

Additional objects, advantages and novel features of the invention will become apparent from the description given herein and the appended claims.

DESCRIPTION OF THE INVENTION

To achieve the foregoing and other objects, and in accordance with the purpose of the present invention, the novel radiopharmaceuticals 1- and 2-$^{11}$C-D-glucose, 1- and 2-$^{11}$C-mannose and 1- and 2-$^{11}$C-D-galactose can be rapidly synthesized by a novel method which comprises condensing the next lower aldose with an alkali metal cyanide, preferably sodium or potassium cyanide at a pH from 7.5 to 9 to produce an aldonitrile which is converted to an epimeric mixture containing the desired aldose by reduction with Raney alloy in hot aqueous formic acid solution. The epimers can be separated by any suitable method. In order to obtain the desired radiopharmaceutical as rapidly as possible, the preferred procedure is high pressure liquid chromatography (HPLC).

Specifically, 1-$^{11}$C-D-glucose and 1-$^{11}$C-D-mannose can be obtained by initially condensing D-arabinose with $^{11}$C-labeled sodium cyanide in aqueous media at pH 7.5 to 9 to produce the corresponding nitriles, reducing the compounds with Raney nickel and separating the resulting 1-$^{11}$C-D-glucose and 1-$^{11}$C-D-mannose by HPLC.

It has been observed that the yield of aldoses in is pH dependent. At pH 7.5–9, the major products are aldoses. However, as the pH increases, the yield of acids increases at the expense of aldehydes.

At the lower pH values, glucose and mannose are the major products from D-arabinose and the glucose to mannose ratio is about 1:2. As the pH increases, aldonic acids become the major products at the expense of glucose and mannose and the ratio of glucose to mannose shifts to 1:1.

$1-^{11}C$-D-galactose is prepared by applying the procedure of the invention to D-lyxose and separating the resulting epimers D-galactose and D-talose.

D-glucose, D-mannose and D-galactose with the $^{11}C$ label at the 2-position are produced by serial application of the procedure to D-erythrose and D-threose respectively. For the second condensation with the alkali cyanide, the carbon atom of the cyanide group is ordinary $^{12}C$. In these syntheses, an intermediate mixture containing $1-^{11}C$-D-ribose and $1-^{11}C$-D-arabinose is obtained when D-erythrose is used as the starting material. The mixture from D-threose contains $1-^{11}C$-D-xylose and $1-^{11}C$-D-lyxose. The compounds $1-^{11}C$-D-arabinose and $1-^{11}C$-D-lyxose are valuable, novel intermediates.

The $^{11}C$ labeled sodium cyanide ($Na^{11}CN$) used in this invention can be prepared from $H^{11}CN$ be reaction with sodium hydroxide or by interchange with $Na^{12}CN$ according to well known procedures. The $H^{11}CN$ can be obtained by subjecting a mixture of nitrogen and hydrogen to irradiation with a beam of protons in accordance with the procedure of U.S. Pat. No. 4,106,982.

The reaction of the selected aldose with the alkali metal $^{11}C$ cyanide is carried out in an aqueous media at a pH of from 7.5 to 9 at ambient temperature (20° C. to 35° C.) during a period of about 10 to 20 minutes. It is preferred to use a molar excess of the cyanide, up to about 4 molar excess, although equimolar quantities of reactants can be employed. The 3 to 4 molar excess is preferred because higher yields of the epimeric mixture are obtained. Generally, the resulting mixtures contain a higher proportion of the desired epimer.

The reaction with the Raney alloy is effected in the presence of 20% to 40% formic acid to convert the cyano group to the aldehyde group. Catalytic amounts of the alloy are employed. The temperature of the reaction is from 100° C. to 120° C. The reaction period is from 10 to 20 minutes.

The radiopharmaceuticals of this invention are especially useful in diagnostic procedures which require following the metabolism of glucose, mannose or galactose. When so employed, a diagnostically effective amount of the selected labeled carbohydrate will be administered, generally parenterally to the individual patient under study, and the course of the metabolism followed using emission tomography.

The following examples are merely illustrative of the invention, and are not to be construed as limiting thereof. Examples 1, 2 and 3, although not carried out with labeled carbon illustrate the utility of the procedure.

The glc analyses were carried out with a Hewlett-Packard 5830A gas chromatography equipped with a thermal conductivity detector. A column [1.8 m×3 mm] containing SE-30 (10%) on Chromosorb 80/199 mesh was employed, with isothermal at 190° and flow of 50 ml/min. HPLC analyses were carried out either with Waters Associated model 6000 liquid chromatography with refractive index detector or with Perkin-Elmer Series 3B liquid chromatographs equipped with LB503 radioactivity monitor. A Bio-Rad HPLC carbohydrate analysis column (Aminex carbohydrate HPX-87, 300 mm×7.8 mm) was employed and eluted with $H_2O$ (85°). IR spectra were determined on a Perkin-Elmer Spectrophotometer 735 B.

EXAMPLE 1

CYANOHYDRIN OF D-ARABINOSE

A solution of 140.21 mg (2.86 m mole) of NaCN in 1 ml of $H_2O$ was adjusted to pH 7.99 with 3 M HOAc and then 178.5 mg (1.19 m mole) of D-arabinose in 1 ml of $H_2O$ were added. The solution was stirred at room temperature for 10 min. and then passed through a column (2×6 cm) of Dowex AG 50 W - X 8 (H+) ion-exchange resin and eluted with water (25 ml). The solution was evaporated to dryness to give 210.7 mg of the cyanohydrin. HPLC (0.4 ml/min.) showed two major peaks at $R_T$16.75 min. and 17.5 min ($R_T$ for arabinose is 19 min.). The cyanohydrins were collected and evaporated $\nu_{max}^{film}$ 2250 cm$^{-1}$ (C≡N), 3300 cm$^{-1}$ (OH).

EXAMPLE 2

GLUCOSE AND D-MANNOSE

A mixture of 700 mg of the product of Example 1 and Raney nickel (1.03 g) in 30% formic acid (45 ml) was stirred for 1 hr. at 100°–110°. The mixture was then cooled to room temperature, passed through celite, and the green solution was evaporated in vacuo to dryness. The residue was dissolved in water, passed through a column (2×17 cm) of Dowex AG50W - X 8 (H+) ion-exchange resin and eluted with water (80 ml). The eluate evaporated to dryness to give 776.2 mg of a mixture of D-glucose and D-mannose. HPLC (0.2 ml/min.) analysis of the mixture showed peaks at $R_T$16.25, 30.5, 33.5 37 and 39.25 min. The first four peaks correspond to aldonic acids, glucose, mannose and unreacted arabinose respectively. The glucose and mannose were isolated by preparative HPLC to give 98 mg of glucose and 164 mg of the mannose which were identified by glc (sily derivative) $R_T$=16 min. ($\alpha$) and 23.31 min ($\beta$) for glucose and 11.52 min. ($\alpha$) and 16.79 min. ($\beta$) for mannose.

EXAMPLE 3

D-GALACTOSE

A solution of 691.44 mg (14.11 m mole) of NaCN in 5 ml of $H_2O$ was adjusted to pH 7.99 with 3 M HOAc (4.3 ml) and then 750.67 mg (5.00 m mole) of D-lyxose in 5 ml of $H_2O$ were added. The solution was stirred at room temperature for 50 min. and then added into the mixture of Raney nickel (1.12 g) in 30% formic acid (45 ml).

The mixture was stirred for 1 hr. at 120° C. Work-up was similar to that for glucose and mannose to give 861.2 mg of mixture. HPLC (0.2 ml/min. analysis of the mixture showed peaks at $R_T$17.6, 33.75, 37.5 and 41 min. These peaks correspond to aldonic acids, galactose, lyxose and talsoe. Galactose (350 mg) was isolated by preparative HPLC and was identified by glc (silyl derivative) $R_T$ = 14.63 min ($\alpha$) and 18.16 ($\beta$).

EXAMPLE 4

1-$^{11}$C-D-GLUCOSE AND 1-$^{11}$C-D-MANNOSE

A solution of 270.45 mg (5.52 m mole) of NaCN in 3 ml of H$_2$O was adjusted to pH 8.0 with 3 M HOAc (1.8 ml). No carrier added (NCA). H$^{11}$CN was transferred on a vacuum line to 300 μl of D-arabinose solution (293.25 mg in 3 ml H$_2$O) and the solution was stirred at room temperature for 10 min. To this was added 0.3 g Raney alloy and 10 ml of 30% HCO$_2$H solution and the mixture was stirred at 110° C. for 10 min. and evaporated to dryness in vaccuo. The residue was dissolved in water (~10 ml), applied to AG 50 W - X 8 column (2×10 cm) and eluted with an additional 10 ml of water. The eluate was evaporated to dryness. The mixture was dissolved in water 200 μl and applied to HPLC equipped with LB503 radioactivity monitor. The compounds 1-$^{11}$C-mannose and 1-$^{11}$C-glucose were separated and collected.

EXAMPLE 5

1-C-D-GALACTOSE

The procedure of Example 4 was repeated using with D-lytose as the starting compound.

EXAMPLE 6 2-$^{11}$C-D-GLUCOSE AND 2-$^{11}$C-D-MANNOSE

The procedure of Example 4 was repeated D-erythose as the starting compound and separating the intermediate D-arabinose and D-ribose. The 1-$^{11}$C-D-arabinose was then utilized as a starting material to produce 2-$^{11}$C-D-glucose and 2-$^{11}$C-D-mannose using the procedure of Example 4, but without labeled HCN.

EXAMPLE 7

2-$^{11}$C-D-GALACTOSE

The procedure of Example 6 was repeated using D-threose as the starting compound and isolating the intermediate 1-$^{11}$C-D-lyxose.

What is claimed is:

1. A novel radiopharmaceutical selected from the group consisting of 1-$^{11}$C-D-glucose, 2-$^{11}$C-D-glucose, 1-$^{11}$C-D-mannose, 2-$^{11}$C-D-mannose, 1-$^{11}$C-D-galactose and 2-$^{11}$C-D-galactose.

2. A compound selected from the group consisting of 1-$^{11}$C-D-arabinose and 1-$^{11}$C-D-lyxose.

3. A method for the preparation of a compound selected from the group consisting of 1-$^{11}$C-D-glucose, 2-$^{11}$C-D-glucose, 1-$^{11}$C-D-mannose, 2-$^{11}$C-D-mannose, 1-$^{11}$C-D-galactose and 2-$^{11}$C-D-galactose which comprises:

(1) for the production of 1-$^{11}$C-D-glucose and 1-$^{11}$C-D-mannose reacting D-arabinose, and for the production of 1-$^{11}$C-D-galactose reacting D-lyxose respectively with an alkali metal cyanide having an $^{11}$C label in an aqueous media at pH 7.5 to 9, reducing resulting cyano compounds with Raney alloy and separating the desired D-glucose and D-mannose compounds from the mixture resulting from the use of D-arabinose as the starting compound and the desired D-galactose from mixture resulting from the use of D-lyxose as the starting compound; and (2) for the production of 2-$^{11}$C-D-glucose or 2-$^{11}$C-D-mannose reacting D-erythrose or for the production of 2-$^{11}$C-galactose reacting D-threose respectively with an alkali metal cyanide having an $^{11}$C label in an aqueous media at pH 7.5 to 9, reducing resulting cyano compounds with Raney alloy and separating 1-$^{11}$C-D-arabinose from the mixture resulting from the use of D-erythrose as the starting compound and 1-$^{11}$C-D-lyxose from the mixture resulting from the use of D-threose as the starting compound, and repeating the same reactions on the said 1-$^{11}$C-D-arabinose and 1-$^{11}$C-D-lyxose except for the use of an alkali metal cyanide with the $^{12}$C isotope of carbon.

4. The method according to claim 3 utilizing sodium cyanide labeled with the $^{11}$C isotope at pH 8.

5. A method for the diagnostic measurement of glucose metabolism wherein a diagnostically effective amount of a compound selected from the group consisting of 1-$^{11}$C-D-glucose, 2-$^{11}$C-D-glucose, 1-$^{11}$C-D-mannose and 2-$^{11}$C-D-mannose is injected into a patient and subsequently imaged.

6. A method for the diagnostic measurement of galactose metabolism wherein a diagnostically effective amount of a compound selected from the group consisting of 1-$^{11}$C-D-galactose and 2-$^{11}$D-galactose is injected into a patient and subsequently imaged.

* * * * *